United States Patent
Egusa et al.

(10) Patent No.: US 11,459,547 B2
(45) Date of Patent: Oct. 4, 2022

(54) METHOD FOR PRODUCING OSTEOBLAST CLUSTER USING HUMAN IPS CELLS

(71) Applicant: TOHOKU UNIVERSITY, Miyagi (JP)

(72) Inventors: Hiroshi Egusa, Miyagi (JP); Hiroko Okawa, Miyagi (JP)

(73) Assignee: TOHOKU UNIVERSITY, Miyagi (JP)

( * ) Notice: Subject to any disclaimer, the term of this patent is extended or adjusted under 35 U.S.C. 154(b) by 359 days.

(21) Appl. No.: 16/497,993

(22) PCT Filed: Mar. 30, 2018

(86) PCT No.: PCT/JP2018/013777
§ 371 (c)(1),
(2) Date: Dec. 23, 2019

(87) PCT Pub. No.: WO2018/181960
PCT Pub. Date: Oct. 4, 2018

(65) Prior Publication Data
US 2020/0385679 A1   Dec. 10, 2020

(30) Foreign Application Priority Data
Mar. 30, 2017 (JP) .............. JP2017-067295

(51) Int. Cl.
*C12N 5/077* (2010.01)
*C12N 5/074* (2010.01)

(52) U.S. Cl.
CPC ......... *C12N 5/0654* (2013.01); *C12N 5/0607* (2013.01); *C12N 2506/45* (2013.01)

(58) Field of Classification Search
None
See application file for complete search history.

(56) References Cited

U.S. PATENT DOCUMENTS

2016/0160180 A1   6/2016   Yamamoto et al.
2016/0287753 A1   10/2016  Egusa

FOREIGN PATENT DOCUMENTS

| JP | 2007-535941 | 12/2007 |
| JP | 2016-49099 | 4/2016 |
| WO | 2005/111197 | 11/2005 |
| WO | 2015/012377 | 1/2015 |
| WO | 2015/064705 | 5/2015 |

OTHER PUBLICATIONS

Zujur et al. "Three-dimensional system enabling the maintenance and directed differentiation of pluripotent stem cells under defined conditions", (May 12, 2017) Cell Biology, vol. 3:e1602875 (Year: 2017).*
International Search Report dated Jul. 3, 2018 in International (PCT) Application No. PCT/JP2018/013777.
Chung et al., "Deferoxamine promotes osteoblastic differentiation in human periodontal ligament cells via the nuclear factor erythroid 2-related factor-mediated antioxidant signaling pathway", Journal of Periodontal Research, 2014, vol. 49, pp. 563-573.
Maeda et al., "Simvastatin Promotes Osteoblast Differentiation and Mineralization in MC3T3-E1 Cells", Biochemical and Biophysical Research Communications, 2001, vol. 280, pp. 874-877.
Kanke et al., "Stepwise Differentiation of Pluripotent Stem Cells into Osteoblasts Using Four Small Molecules under Serum-free and Feeder-free Conditions", Stem Cell Reports, 2014, vol. 2, pp. 751-760.

* cited by examiner

*Primary Examiner* — Teresa E Knight
(74) *Attorney, Agent, or Firm* — Wenderoth, Lind & Ponack, L.L.P.

(57) ABSTRACT

The present invention provides a method of producing an osteoblast construct from human iPS cells, the method including the steps of: (1) inducing formation of an embryoid body by subjecting undifferentiated human iPS cells to non-adherent culture; (2) inducing differentiation of the human iPS cells into mesodermal cells by subjecting the embryoid body of the human iPS cells obtained in the step (1) to non-adherent culture; and (3) inducing differentiation into osteoblasts by subjecting the mesodermal cells of the human iPS cells obtained in the step (2) to non-adherent culture.

6 Claims, 7 Drawing Sheets

METHOD FOR PRODUCING OSTEOBLAST CLUSTER USING HUMAN IPS CELLS

TECHNICAL FIELD

The present invention relates to a method of generating an osteoblast construct using iPS cells.

BACKGROUND ART

There is an extremely high demand for an artificial bone/bone substitute material for replacing, for example, a defective site where bone has been lost due to bone tumor excision, comminuted fracture, bone defect associated with fixation in rheumatoid arthritis, alveolar ridge resorption, or the like.

Non-absorptive materials, such as hydroxyapatite, and absorptive materials, such as β-tricalcium phosphate, which are currently in clinical use as artificial bones/bone substitute materials, have a problem of, for example, being inferior to autologous bones in osteoinductive activity, and do not alwaysprovide good prognosis in surgical intervention. In addition, a hybrid artificial bone/bone substitute material obtained by combining an artificial bone and a growth factor protein, such as a bone morphogenetic protein (BMP), which is a next-generation type whose further development is desired, lacks an "extracellular matrix", which is important for bone tissue regeneration, and hence has not been able to provide a sufficient bone regeneration effect.

Under such circumstances, one of the inventors of the present invention has succeeded in generating a bone regeneration agent including an inactivated cell construct derived from stem cells as a source material, the inactivated cell construct containing at least a mineral and an extracellular matrix (Patent Literature 1).

CITATION LIST

Patent Literature

PTL 1: WO 2015/064705 A1

Non-patent Literature

NPL 1: Stem Cell Reports Vol. 2, 751-760, Jun. 3, 2014

SUMMARY OF INVENTION

Technical Problem

An object of the present invention is to provide a three-dimensional and solid osteoblast construct using human iPS cells as a source material.

Solution to Problem

Under the above-mentioned circumstances, the inventors of the present invention generated an osteoblast construct using human iPS cells as a source material by a method involving culturing the cells in an ES medium for 2 days, further culturing the cells with the addition of retinoic acid for 2 days, and culturing the cells in an osteoblastic differentiation induction medium in accordance with a method described in Patent Literature 1. As a result, a cell construct was obtained unlike the case of using mouse iPS cells, but the cell construct had a hollow bag-like (sac-like) shape. In addition, also when the addition of retinoic acid was omitted in the above-mentioned method, the cell construct similarly had a hollow bag-like shape. Meanwhile, in Non-patent Literature 1, there is a description that an osteoblast construct was produced by subjecting human iPS cells to adherent culture in a mesodermal cell differentiation induction medium, and subjecting the cells to adherent culture in an osteoblastic differentiation induction medium, without performing a step of inducing formation of an embryoid body. However, cells obtained by the method described in Non-patent Literature 1 proliferate two-dimensionally along the wall surface of a culture vessel, and hence cannot be collected as a three-dimensional cell construct to serve as a source material for an artificial bone/bone substitute material. Accordingly, when the inventors of the present invention performed culture in accordance with the method described in Non-patent Literature 1 except that non-adherent culture was performed, the non-adherent culture caused cell death, and hence the required cell construct was not able to be obtained. On the basis of those newly found results, the inventors of the present invention have further made extensive investigations, and as a result, have found that an osteoblast construct that is not bag-like can be obtained from human iPS cells even in non-adherent culture through the following three steps: a step of inducing formation of an embryoid body; a step of inducing differentiation of the embryoid body obtained in the above-mentioned step into mesodermal cells; and a step of inducing differentiation of the mesodermal cells obtained in the above-mentioned step into osteoblasts. The inventors of the present invention have further made minute investigations on culture conditions and the like on the basis of the novel finding, and thus have completed the present invention.

Therefore, the present invention provides a method as described in any one of the following items.

Item 1. A method of producing an osteoblast construct from human iPS cells, the method including the steps of: (1) inducing formation of an embryoid body by subjecting undifferentiated human iPS cells to non-adherent culture; (2) inducing differentiation of the human iPS cells into mesodermal cells by subjecting the embryoid body of the human iPS cells obtained in the step (1) to non-adherent culture; and (3) inducing differentiation into osteoblasts by subjecting the mesodermal cells of the human iPS cells obtained in the step (2) to non-adherent culture.

Item 2. The method according to Item 1, wherein the method excludes a method involving using a medium having blended therein only retinoic acid as a component for inducing differentiation into mesoderm in the step (2).

Item 3. The method according to Item 1 or 2, wherein a culture time in the step (1) is from 0.5 day to 3.5 days.

Item 4. The method according to any one of Items 1 to 3, wherein the culture in the step (2) is performed in the presence of at least one kind selected from the group consisting of a Wnt signal activator and a Hedgehog signal inhibitor.

Item 5. The method according to Item 4, wherein the Wnt signal activator is at least one kind selected from the group consisting of, for example, CHIR99021, 6-bromoindirubin-3'-oxime (BIO), kenpaullone, SB-216763, SKL2001, deoxycholic acid, WAY-316606, NSC-693868, ricinine, 7-oxo-β-sitosterol, IM-12, and HLY78.

Item 6. The method according to Item 4 or 5, wherein the Hedgehog signal inhibitor is at least one kind selected from the group consisting of, for example, cyclopamine, AY9944, GANT58, GANT61, jervine, SANT-1, SANT-2, U18666A, veratramine, vismodegib, Cur-61414, robotnikinin, JK184, and HPI-4.

Item 7. The method according to any one of Items 1 to 6, wherein the culture in the step (3) is performed in the presence of at least one kind selected from the group consisting of a hypoxia-mimetic compound and a statin compound.

Item 8. A method of producing a bone regeneration agent, including the steps of: producing an osteoblast construct from human iPS cells by the method of any one of Items 1 to 7; and subjecting the osteoblast construct to inactivation treatment.

Advantageous Effects of Invention

According to the present invention, the three-dimensional osteoblast construct can be obtained from human iPS cells by using non-adherent culture. In addition, according to the present invention, the solid osteoblast construct that is not bag-like can be obtained.

DESCRIPTION OF EMBODIMENTS

Method of Producing Osteoblast Construct

Figure 1:
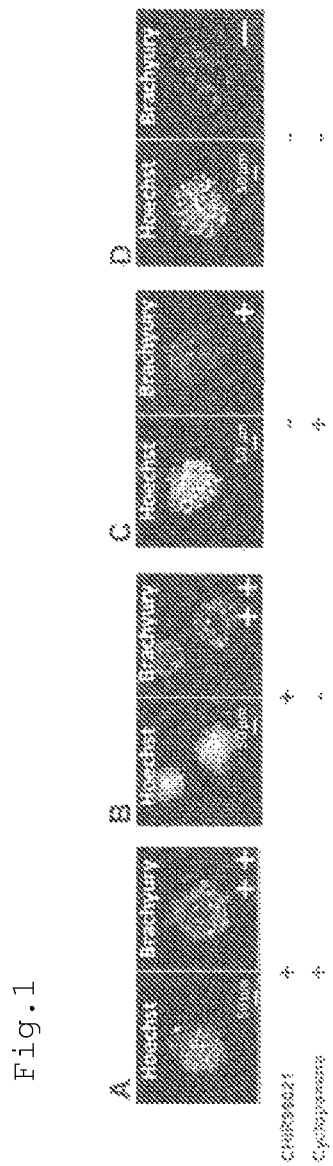
FIG. 1 are photographs for showing the results of immunofluorescent staining for evaluating the formation of mesoderm cell constructs in Examples of the present application.

The present invention provides a method of producing an osteoblast construct from human iPS cells, the method including the steps of: (1) inducing formation of an embryoid body by subjecting undifferentiated human iPS cells to non-adherent culture; (2) inducing differentiation of the human iPS cells into mesodermal cells by subjecting the embryoid body of the human iPS cells obtained in the step (1) to non-adherent culture; and (3) inducing differentiation into osteoblasts by subjecting the mesodermal cells of the human iPS cells obtained in the step (2) to non-adherent culture.

(1) Induction of Embryoid Body Formation

The method of the present invention includes the step of inducing formation of an embryoid body by subjecting undifferentiated human iPS cells to non-adherent culture.

As the human iPS cells to be used as a source material, human iPS cells generated by introducing a nuclear reprogramming substance into somatic cells may be used.

The somatic cells that may be used as a source material for the generation of the iPS cells may be any cells of human origin except germ cells, and examples thereof include oral mucosal cells (e.g., gingival fibroblasts, buccal mucosal fibroblasts, gingival epithelial cells, and buccal mucosal epithelial cells), keratinized epithelial cells (e.g., keratinized epidermal cells), mucosal epithelial cells (e.g., epithelial cells in the lingual epithelium), exocrine gland epithelial cells (e.g., mammary gland cells), hormone-secreting cells (e.g., adrenomedullary cells), metabolizing or storage cells (e.g., hepatocytes), luminal epithelial cells constituting boundary surfaces (e.g., type I alveolar cells), luminal epithelial cells in the closed circulatory system (e.g., vascular endothelial cells), cells with motile cilia (e.g., airway epithelial cells), extracellular matrix-secreting cells (e.g., fibroblasts), contractile cells (e.g., smooth muscle cells), hematopoietic and immune cells (e.g., T lymphocytes), sensory cells (e.g., rod cells), autonomic neurons (e.g., cholinergic neurons), supporting cells for sensory organs and peripheral neurons (e.g., satellite cells), neuronal cells and glial cells in the central nervous system (e.g., astroglial cells), pigment cells (e.g., retinal pigment epithelial cells), and progenitor cells thereof (e.g., tissue progenitor cells). The level of differentiation of the cells is not particularly limited, and both undifferentiated progenitor cells (including somatic stem cells) and terminally differentiated mature cells may be similarly used as a source for the somatic cells in the present invention. Herein, examples of the undifferentiated progenitor cells include tissue stem cells (somatic stem cells), such as neural stem cells, hematopoietic stem cells, mesenchymal stem cells, and dental pulp stem cells.

In the present invention, the "nuclear reprogramming substance" may include any substance (set of substances) capable of inducing iPS cells from somatic cells, such as a protein factor or a nucleic acid encoding the protein factor (including a form of being incorporated into a vector), or a low-molecular-weight compound. When the nuclear reprogramming substance is a protein factor or a nucleic acid encoding the protein factor, preferred examples thereof include the following combinations (only the names of protein factors are given in the following description).

[1] Oct3/4, Klf4, and c-Myc
[2] Oct3/4, Klf4, c-Myc, and Sox2 (herein, Sox2 may be replaced with Sox1, Sox3, Sox15, Sox17, or Sox18. In addition, Klf4 may be replaced with Klf1, Klf2, or Klf5. Further, c-Myc may be replaced with T58A (active mutant), N-Myc, or L-Myc.)
[3] Oct3/4, Klf4, c-Myc, Sox2, Fbx15, Nanog, Eras, ECAT15-2, Tcl1, and β-catenin (active mutant S33Y)
[4] Oct3/4, Klf4, c-Myc, Sox2, TERT, and SV40 Large T antigen (hereinafter referred to as SV40LT)
[5] Oct3/4, Klf4, c-Myc, Sox2, TERT, and HPV16 E6
[6] Oct3/4, Klf4, c-Myc, Sox2, TERT, and HPV16 E7
[7] Oct3/4, Klf4, c-Myc, Sox2, TERT, HPV6 E6, and HPV16 E7
[8] Oct3/4, Klf4, c-Myc, Sox2, TERT, and Bmil (see WO 2007/069666 A1 for the above-mentioned combinations (provided that, in the above-mentioned combination [2], see Nature Biotechnology, 26, 101-106 (2008) for the replacement of Sox2 with Sox18 or the replacement of Klf4 with Klf1 or Klf5). See also Cell, 126, 663-676 (2006), Cell, 131, 861-872 (2007), and the like for the combination of "Oct3/4, Klf4, c-Myc, and Sox2". See also Nat. Cell Biol., 11, 197-203 (2009) for the combination of "Oct3/4, Klf2 (or Klf5), c-Myc, and Sox2". See also Nature, 451, 141-146 (2008) for the combination of "Oct3/4, Klf4, c-Myc, Sox2, hTERT, and SV40LT".)
[9] Oct3/4, Klf4, and Sox2 (see Nature Biotechnology, 26, 101-106 (2008))
[10] Oct3/4, Sox2, Nanog, and Lin28 (see Science, 318, 1917-1920 (2007))
[11] Oct3/4, Sox2, Nanog, Lin28, hTERT, and SV40LT (see Stem Cells, 26, 1998-2005 (2008))
[12] Oct3/4, Klf4, c-Myc, Sox2, Nanog, and Lin28 (see Cell Research (2008) 600-603)
[13] Oct3/4, Klf4, c-Myc, Sox2, and SV40LT (see also Stem Cells, 26, 1998-2005 (2008))
[14] Oct3/4 and Klf4 (see Nature 454: 646-650 (2008), Cell Stem Cell, 2: 525-528 (2008)))
[15] Oct3/4 and c-Myc (see Nature 454: 646-650 (2008))
[16] Oct3/4 and Sox2 (see Nature, 451, 141-146 (2008), WO 2008/118820 A2)
[17] Oct3/4, Sox2, and Nanog (see WO 2008/118820 A2)
[18] Oct3/4, Sox2, and Lin28 (see WO 2008/118820 A2)
[19] Oct3/4, Sox2, c-Myc, and Esrrb (herein, Essrrb may be replaced with Esrrg. See Nat. Cell Biol., 11, 197-203 (2009))
[20] Oct3/4, Sox2, and Esrrb (see Nat. Cell Biol., 11, 197-203 (2009))
[21] Oct3/4, Klf4, and L-Myc
[22] Oct3/4 and Nanog
[23] Oct3/4
[24] Oct3/4, Klf4, c-Myc, Sox2, Nanog, Lin28, and SV40LT (see Science, 324: 797-801 (2009))
[25] Oct3/4, Klf4, Sox2, and GLIS family members (there are given, for example, GLIS1, GLIS2, and GLIS3, and there is suitably given GLIS family zinc finger 1 (GLIS1). See WO 2010/098419 A1 and WO 2011/102531 A2)
[26] Oct3/4, Klf4, Sox2, and IRX family members (there are given, for example, IRX1, IRX2, IRX3, IRX4, IRX5, and IRX6, and there is suitably given iroquois homeobox protein 6 (IRX6). See WO 2010/098419 A1)
[27] Oct3/4, Klf4, Sox2, and PTX family members (there are given, for example, PITX1, PITX2, and PITX3, and there is suitably given paired-like homeodomain transcription factor 2 (PITX2). Three isoforms (isoforms a, b, and c) are known as PITX2 and any of the isoforms may be used, and isoform b is particularly preferred. See WO 2010/098419 A1)
[28] Oct3/4, Klf4, Sox2, and DMRT-like family B with proline-rich C-terminal 1 (DMRTB1, see WO 2010/098419 A1)

In the above-mentioned combinations [1] to [28], any other Oct family member, such as Oct1A or Oct6, may be used instead of Oct3/4. In addition, any other Sox family member, such as Sox7, may be used instead of Sox2 (or Sox1, Sox3, Sox15, Sox17, or Sox18). Further, any other Lin family member, such as Lin28b, may be used instead of Lin28.

In addition, combinations which are not exactly the same as any one of the above-mentioned combinations [1] to [28] but contain all the components in any one of the above-mentioned combinations [1] to [28] and further contain any other substance may also be included in the category of the "nuclear reprogramming substance" in the present invention. In addition, under such a condition that some of the components in any one of the above-mentioned combinations [1] to [28] are endogenously expressed in the somatic cells to be subjected to nuclear reprogramming at a level sufficient for nuclear reprogramming, a combination of only the components other than the above-mentioned components may also be included in the category of the "nuclear reprogramming substance" in the present invention.

Of those combinations, a preferred example of the nuclear reprogramming substance is at least one, preferably two or more, more preferably three or more selected from Oct3/4, Sox2, Klf4, c-Myc, Nanog, Lin28, and SV40LT.

Human cDNA sequence information on the above-mentioned nuclear reprogramming substances may be acquired with reference to NCBI accession numbers described in WO 2007/069666 A1 or WO 2010/098419 A1 (Nanog is described under the name "ECAT4" in these publications. Human cDNA sequence information on Lin28, Lin28b, Esrrb, Esrrg, and L-Myc may be acquired with reference to respective NCBI accession numbers shown in Table 1 below.). A person skilled in the art could easily isolate cDNAs thereof.

TABLE 1

| Gene name | NCBI accession numbers |
| --- | --- |
| Lin28 | NM_024674 |
| Lin28b | NM_001004317 |
| Esrrb | NM_004452 |
| Esrrg | NM_001438 |
| L-Myc | NM_001033081 |

In addition, human cDNA sequence information on GLIS family members, IRX family members, PTX family members, and DMRTB1 may be acquired with reference to respective NCBI accession numbers shown in Table 2 below.

TABLE 2

| | NCBI accession numbers | |
| --- | --- | --- |
| Gene name | cDNA | Protein |
| IRX1 | NM_010573 | NP_034703 |
| IRX2 | NM_010574 | NP_034704 |
| IRX3 | NM_008393 | NP_032419 |
| IRX4 | NM_018885 | NP_061373 |

TABLE 2-continued

| Gene name | NCBI accession numbers | |
| --- | --- | --- |
| | cDNA | Protein |
| IRX5 | NM_018826 | NP_061296 |
| IRX6 | NM_022428 | NP_071873 |
| GLIS1 | NM_147221 | NP_671754 |
| GLIS2 | NM_031184 | NP_112461 |
| GLIS3 | NM_175459 | NP_780668 |
| PITX1 | NM_011097 | NP_035227 |
| PITX2 (isoform a) | NM_001042504 | NP_001035969 |
| PITX2 (isoform b) | NM_011098 | NP_035228 |
| PITX2 (isoform c) | NM_001042502 | NP_001035967 |
| PITX3 | NM_008852 | NP_032878 |
| DMRTBI | XM_205469 | XP_205469 |

In addition, a native or artificial mutant protein which has 90% or more, preferably 95% or more, more preferably 98% or more, particularly preferably 99% or more identity to any of the above-mentioned amino acid sequences, and has a comparable nuclear reprogramming ability as a substitute factor of Klf4 as compared to a wild-type protein, and a nucleic acid encoding the mutant protein may also be utilized as a nuclear reprogramming substance of the present invention in place of Klf4.

When the protein factor itself is used as the nuclear reprogramming substance, the protein factor may be prepared by inserting the obtained cDNA into an appropriate expression vector, introducing the expression vector into host cells, culturing the cells, and collecting a recombinant protein factor from the resultant culture. Meanwhile, when the nucleic acid encoding the protein factor is used as the nuclear reprogramming substance, an expression vector is constructed by inserting the obtained cDNA into a viral vector, a plasmid vector, an episomal vector, or the like, and is subjected to a nuclear reprogramming step.

For the introduction of the nuclear reprogramming substance into the somatic cells, a method used in the technical field to which the present invention belongs, such as the method of Patent Literature 1 (WO 2015/64705 A1), may be appropriately used.

In addition, the iPS cells may be obtained by using a factor, such as C4ORF51, HHLA1, ABHD12B, or ZNF541, as an indicator for differentiation resistance, and selecting a line in which such factor is not significantly expressed (see WO 2013/014929 A1).

In addition, the iPS cells to be used may be obtained by, for example, performing culture with feeder cells that supply soluble factors required for, for example, the survival, proliferation, and undifferentiation maintenance of cells and serve as scaffolds for cell adhesion, and appropriately removing the feeder cells as appropriate before embryoid body formation induction.

This step may be performed by subjecting those undifferentiated iPS cells to non-adherent culture in a liquid medium to be used for inducing the formation of an embryoid body.

Figure 4:
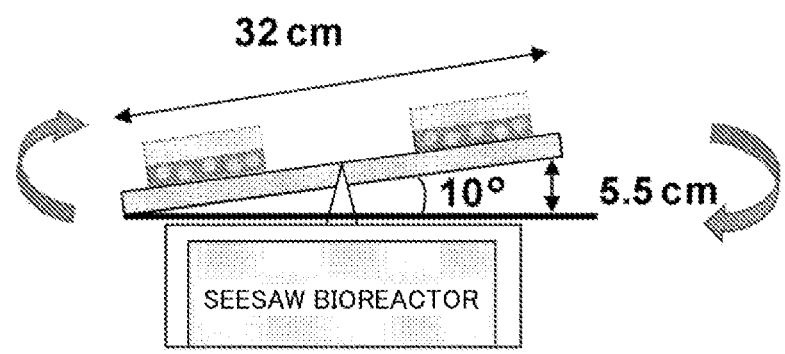
FIG. 4 is an illustration of the outline of a seesaw bioreactor used in Examples of the present application.

In the present invention, the "non-adherent culture" means culturing under a state in which the adhesion of cells to the bottom surface and the like (e.g., bottom surface and wall surface) of a culture vessel is suppressed. In the present invention, the non-adherent culture encompasses, for example, shaking culture, and static culture using a non-adherent culture vessel in which the adhesion of cells to the bottom surface and the like of the culture vessel is suppressed (e.g., a non-adherent culture dish, a non-adherent well, a non-adherent flask, a three-dimensional culture plate, or a cell construct generation vessel). As the non-adherent culture vessel, for example, a vessel subjected to low-attachment surface treatment by means of a phospholipid gel, a hydrogel, fine processing, or the like may be used. In addition, in the present invention, for the shaking culture, the above-mentioned non-adherent culture vessel may be used, or a culture vessel that is not non-adherent may be used. When the shaking culture is performed, a method therefor is not particularly limited, but the shaking culture may be performed, for example, using such a seesaw bioreactor as illustrated in FIG. 4. In addition, the inclination angle of the shaking culture is not particularly limited, but is preferably from 1° to 40°, more preferably from 5° to 35°, still more preferably from 10° to 30° against a horizontal direction. The amplitude of the shaking culture is not particularly limited, but may be, for example, from about 0.1 cm to about 20 cm. The cycle of shaking is not particularly limited, but may be, for example, from about 0.01 Hz to about 1.00 Hz. In FIG. 4, the inclination angle is 10°, and the amplitude is 5.5 cm. The width of a table on which a culture flask is to be placed (member of the seesaw bioreactor) is not particularly limited, and a table having a width in the range of, for example, from 20 cm to 50 cm, or from 30 cm to 40 cm may be used. The table culture flask is not particularly limited, but a flask having a culture area (growth area) in the range of, for example, from 5 cm$^2$ to 200 cm$^2$, from 10 cm$^2$ to 60 cm$^2$, or from 15 cm$^2$ to 35 cm$^2$ may be used. In the case where the shaking culture is performed, a cell concentration at the start of the culture is not particularly limited, but when a culture flask having a growth area of 25 cm$^2$ is used, the cell concentration is preferably from about 1×10$^2$ cells/flask to about 1×10$^8$ cells/flask, more preferably from about 1×10$^6$ cells/flask to about 7×10$^6$ cells/flask.

As the medium, a medium for culturing primate ES/iPS cells may be appropriately used. In the present invention, a medium for culturing ES cells is sometimes referred to simply as ES medium. Examples of the medium for culturing primate ES/iPS cells include: RCHEMD001 manufactured by ReproCELL Inc.; NutriStem manufactured by Biological Industries; and Essential 6 Medium or StemFlex Medium manufactured by ThemoFisher Scientific. Such medium may have blended therein growth factors, such as fibroblast growth factors (FGF). Those growth factors may be used alone or in combination thereof. In addition, the medium may have blended therein an additive that may be used in cell culture of stem cells or the like, as required. Specific examples of such additive include fetal bovine serum, amino acids (e.g., L-glutamine), and antibiotics (e.g., penicillin, streptomycin, and amphotericin B).

A culture time in this step is, for example, preferably from about 0.5 day to about 3.5 days, more preferably from 0.625 day to 2.5 days, still more preferably from 0.875 day to 1.25 days. In addition, the culture time in this step is, for example, preferably from about 12 hours to about 84 hours, more preferably from about 15 hours to about 60 hours, still more preferably from about 21 hours to about 30 hours. A case in which the culture time in this step is set within the above-mentioned range is preferred because a final osteoblast construct can be obtained in a solid shape that is not bag-like. A culture temperature in this step is not particularly limited, and is, for example, preferably from 30° C. to 42° C., more preferably from 35° C. to 39° C. The culture in this step is preferably performed under an atmosphere of 3% to 10% CO$_2$.

Through this step, the undifferentiated human iPS cells are first grown into an embryoid body instead of directly culturing undifferentiated human iPS cells in a mesodermal cell induction medium as in Non-patent Literature 1, and as a result, cell death in the next step for induction into mesodermal cells can be significantly suppressed.

Therefore, in the method of the present invention, it is intended that the embryoid body formation step serving as the step (1) does not substantially cause mesodermal cell induction, and does not proceed beyond the formation of an embryoid body. Therefore, a medium free of an inducer into mesodermal cells is typically used as the medium to be used in the step (1).

(2) Induction of Differentiation into Mesodermal Cells

The method of the present invention includes the step of inducing differentiation of the human iPS cells into mesodermal cells by subjecting the embryoid body of the human iPS cells obtained in the above-mentioned step (1) to non-adherent culture.

As a medium to be used in this step, a medium suitable for differentiation induction of mesodermal cells may be appropriately used. Examples of such medium include: a DMEM medium manufactured by Nacalai Tesque Inc.; a DMEM/F12 medium manufactured by Thermo Fisher Scientific; a Neurobasal medium manufactured by Thermo Fisher Scientific; an RPMI 1640 medium manufactured by Thermo Fisher Scientific; and a Stemline™ II hematopoietic stem cell growth medium manufactured by Sigma-Aldrich Corporation. Those media may be used alone or in combination thereof.

The medium to be used in this step preferably has blended therein a Wnt signal activator from the viewpoint of promoting the induction of differentiation into mesoderm. The Wnt signal activator is not particularly limited, but examples thereof include CHIR99021, 6-bromoindirubin-3'-oxime (BIO), Kenpaullone, SB-216763, SKL2001, deoxycholic acid, WAY-316606, NSC-693868, ricinine, 7-oxo-β-sitosterol, IM-12, and HLY78. Of those, CHIR99021 or the like is preferred. Those Wnt signal activators may be used alone or in combination thereof.

When the Wnt signal activator is blended, its blending amount is not particularly limited, but is, for example, preferably from 1 µM to 100 µM, more preferably from 10 µM to 50 µM in terms of final concentration in the medium to be used in this step.

The medium to be used in this step preferably has blended therein a Hedgehog signal inhibitor from the viewpoint of promoting the induction of differentiation into mesoderm. The Hedgehog signal inhibitor is not particularly limited, but examples thereof include cyclopamine, AY9944, GANT58, GANT61, jervine, SANT-1, SANT-2, U18666A, veratramine, Vismodegib, Cur-61414, Robotnikinin, JK184, and HPI-4. Of those, cyclopamine or the like is preferred. Those Hedgehog signal inhibitors may be used alone or in combination thereof.

When the Hedgehog signal inhibitor is blended, its blending amount is not particularly limited, but is, for example, preferably from 1 µM to 100 µM, more preferably from 1 µM to 10 µM in terms of final concentration in the medium to be used in this step.

In the present invention, it is preferred to use both the Wnt signal activator and the Hedgehog signal inhibitor.

As described in "Solution to Problem" above, the present invention has been completed by making further improvements on the basis of the following novel finding in order to solve the problem involved in the finding: a cell construct obtained by the method involving culture in an ES medium for 2 days, further culture with the addition of retinoic acid for 2 days, and culture in an osteoblastic differentiation induction medium in accordance with the method described in Patent Literature 1 has a hollow bag-like shape. Therefore, a method involving a culture step using a medium having blended therein only retinoic acid as a component capable of inducing differentiation into mesoderm after the step of inducing embryoid body formation is excluded from the method of the present invention.

In addition, the medium may have blended therein an additive that may be used in cell culture, as required. Specific examples of such additive include fetal bovine serum, amino acids (e.g., L-glutamine), and antibiotics (e.g., penicillin, streptomycin, and amphotericin B).

In addition, the medium may be supplemented with, for example, a commercially available supplement for cell culture as an additive to be used for cell culture. Examples of such supplement include: N-2 Supplement manufactured by Thermo Fisher Scientific; B-27 Supplement manufactured by Thermo Fisher Scientific; Insulin, Transferrin, Selenium Solution manufactured by Thermo Fisher Scientific; Wnt 3a manufactured by R&D Systems; Activin A manufactured by R&D Systems; and BMP4 manufactured by PeproTech. Those supplements may be used alone or in combination thereof.

The method of the present invention is a method for producing a cell construct of osteoblasts. Therefore, this mesodermal cell differentiation induction step is also performed by non-adherent culture. Specific modes of the non-adherent culture include the above-mentioned ones. In this step, static culture using a non-adherent culture vessel (e.g., a non-adherent culture dish, a non-adherent well, or a non-adherent flask) or the like is preferred.

A culture time in this step is, for example, preferably from 0.125 day to 10 days, more preferably from 1 day to 8 days, still more preferably from 3 days to 6 days. In addition, the culture time in this step is, for example, preferably from about 3 hours to about 240 hours, more preferably from about 24 hours to about 192 hours, still more preferably from about 72 hours to about 144 hours. A culture temperature in this step is not particularly limited, and is, for example, preferably from 30° C. to 42° C., more preferably 35° C. to 39° C. The culture in this step is preferably performed under an atmosphere of 3% to 10% $CO_2$.

In the present invention, it is important for obtaining a solid cell construct from human iPS cells as a source material that the step of inducing differentiation into mesodermal cells be performed between the step (1) of inducing embryoid body formation described above and the step (3) of inducing differentiation into osteoblasts described below.

(3) Induction of Differentiation into Osteoblasts

The method of the present invention includes the step of inducing differentiation into osteoblasts by subjecting the mesodermal cells of the human iPS cells obtained in the step (2) to non-adherent culture.

As a medium to be used in this step, a medium suitable for the induction of differentiation into osteoblasts may be appropriately used. Examples of such medium include: a DMEM medium (e.g., sodium pyruvate-free DMEM medium manufactured by Nacalai Tesque); and an αHEM medium (e.g., αHEM medium manufactured by Nacalai Tesque). Those media may be used alone or in combination thereof.

In this step, the medium may have blended therein an osteoblastic differentiation induction-promoting agent or the like. Examples of the osteoblastic differentiation induction-promoting agent include ascorbic acid, β-glycerophosphoric acid, dexamethasone, BMP-2, hydrocortisone hemisuccinate, and retinoic acid. The ascorbic acid may be ascorbic acid 2-phosphate or a salt thereof. In addition, as a differentiation inducer, instead of or in addition to dexamethasone, hydrocortisone hemisuccinate may be used. Those osteoblastic differentiation induction-promoting agents may be used alone or in combination thereof.

When ascorbic acid is blended, its blending amount is not particularly limited, but is, for example, preferably from 50 µM to 300 µM, more preferably from 150 µM to 200 µM in terms of final concentration in the medium to be used in this step. When β-glycerophosphoric acid is blended, its blending amount is not particularly limited, but is, for example, preferably from 1 mM to 100 mM, more preferably from 5 mM to 15 mM in terms of final concentration in the medium to be used in this step. When dexamethasone is blended, its blending amount is not particularly limited, but is, for example, preferably from 0.001 µM to 10 µM more preferably from 0.01 µM to 1.0 µM in terms of final concentration in the medium to be used in this step.

From the viewpoint of mineralization of osteoblasts, the medium in this step preferably further has blended therein a hypoxia-mimetic compound. Examples of the hypoxia-mimetic compound include desferrioxamine (DFX) and cobalt chloride ($CoCl_2$). Those hypoxia-mimetic compounds may be used alone or in combination thereof.

From the viewpoint of mineralization of osteoblasts, the medium in this step preferably further has blended therein a statin compound. Examples of the statin compound include atorvastatin, fluvastatin, simvastatin, lovastatin, pitavastatin, pravastatin, and rosuvastatin. Those statin compounds may be used alone or in combination thereof.

In addition, the medium may have blended therein an additive that may be used in cell culture, as required. Specific examples of such additive include fetal bovine serum, amino acids (e.g., L-glutamine), and antibiotics (e.g., penicillin, streptomycin, and amphotericin B).

The method of the present invention is a method for producing a cell construct of osteoblasts. Therefore, this mesodermal cell differentiation induction step is also performed by non-adherent culture. Specific modes of the non-adherent culture include the above-mentioned ones. In this step, shaking culture or the like is preferred.

A culture time in this step is, for example, preferably from about 1 day to about 90 days, more preferably from about 7 days to about 60 days, still more preferably from about 21 days to about 50 days. In addition, the culture time in this step is, for example, preferably from about 24 hours to about 2,160 hours, more preferably from about 168 hours to about 1,440 hours, still more preferably from about 504 hours to about 1,200 hours. A culture temperature in this step is not particularly limited, and is, for example, preferably from 30° C. to 42° C., more preferably from 35° C. to 39° C. The culture in this step is preferably performed under an atmosphere of 3% to 10% $CO_2$.

Method of Producing Bone Regeneration Agent

The present invention also provides a method of producing a bone regeneration agent, including the steps of: producing an osteoblast construct from human iPS cells by the above-mentioned method; and subjecting the osteoblast construct to inactivation treatment.

The human iPS cells serving as a source material to be used in the step of producing an osteoblast construct, and treatment and the like required in the step of producing an osteoblast construct are as described above.

The method of the present invention includes the step of subjecting the osteoblast construct obtained by the above-mentioned step to inactivation treatment.

A method for the inactivation is not particularly limited, but examples thereof include freeze-drying, heat treatment, high-pressure treatment, acid or alkali solution treatment, high-pressure steam sterilization, radiation sterilization, gas sterilization, and electromagnetic wave treatment. Conditions for the freeze-drying are not particularly limited, and a known method may be used. In addition, for example, preliminary freezing may be performed before the freeze-drying. The temperature of the preliminary freezing is not particularly limited, but is preferably, for example, from about $-12°$ C. to about $-20°$ C. A freeze-drying temperature is not particularly limited, but is preferably from about $-100°$ C. to about $-5°$ C. In addition, a freeze-drying pressure is not particularly limited, and is, for example, preferably 600 Pa or less, more preferably 50 Pa or less. As specific freeze-drying conditions, there is given, for example, a method involving gradually decreasing the pressure to from 5 Pa to 20 Pa, the decrease starting simultaneously with the start of freeze-drying, at a fixed temperature of $-10°$ C.

Now, the present invention is more specifically described by way of Examples and Comparative Example. However, the present invention is not limited thereto.

EXAMPLES (1-1) Culture of Human iPS Cells

For an experiment, a human skin fibroblast-derived iPS cell line (409B2: RIKEN BRC CELL BANK) was used. SNLP76.7-4 cells (provided by Dr. Allan Bradley of the Sanger Institute, UK) were used as feeder cells.

SNLP76.7-4 feeder cells were seeded in a 10 cm cell culture plate (coated with 0.1% gelatin), and cultured using a DMEM medium (sodium pyruvate-free: Nacalai Tesque, Cat. #08459-35)] containing 7% fetal bovine serum (FBS: Japan Bio Serum, Lot #JBS-011501), 2 mM L-glutamine (Thermo Fisher Scientific, Cat. #25030-081), 50 U penicillin, and 50 µg/ml streptomycin (Thermo Fisher Scientific, Cat. #15140-122). The medium was changed every 2 days. Before the culture of iPS cells, the SNLP76.7-4 feeder cells were treated with 12 µg/ml mitomycin C (Nacalai Tesque, Cat. #20898-21) for 2.5 hours, and seeded in a 10 cm cell culture plate (coated with 0.1% gelatin) at a concentration of $1.5 \times 10^6$ cells/dish.

iPS cells were seeded on the SNLP76.7-4 feeder cells, and cultured using Primates ES Medium (ES medium: REPROCELL, RCHEMD001) containing 4 ng/ml human basic FGF (REPROCELL, RCHEOT002, 003). The medium was changed every day.

(1-2) Formation of Embryoid Bodies

The iPS cells were washed with phosphate buffered saline (PBS), and treated with 1 ml of a CTK solution (0.25% trypsin, 0.1 mg/ml collagenase IV, 10 mM CaCl2), 20% KSR) at 37° C. for 1 minute. After that, the CTK solution was removed by aspiration, and 1 ml of PBS was added. PBS was removed, and only the feeder cells exfoliated from the culture plate were removed by aspiration as much as possible. After that, adherent iPS cells remaining in the culture plate were collected using 5 ml of ES medium (RCHEMD001) supplemented with 4 ng/ml FGF. The resultant cell suspension was transferred to a low-attachment culture dish (Thermo Fisher Scientific, Cat. #150239), and subjected to static culture for 1 day to induce the formation of embryoid bodies. As a control, the formation of embryoid bodies was performed for 0 days or 4 days.

(1-3) Induction of Differentiation into Mesoderm Cells

After static culture had been performed for 1 day, iPS cell embryoid bodies were collected. The collected iPS cell embryoid bodies were seeded on a fresh low-attachment culture dish and subjected to static culture for 5 days using 5 ml of a mesoderm differentiation induction medium [1:1 mixed medium of DMEM/F12 (Thermo Fisher Scientific, Cat. #11330-032) and Neurobasal medium (Thermo Fisher Scientific, Cat. #21103-049) containing 2% B-27 Supplement (Thermo Fisher Scientific, Cat. #17504-044), 1% N-2 Supplement (Thermo Fisher Scientific, Cat. #17502-048), 30 CHIR99021 (Wako Pure Chemical Industries, Ltd., Cat. #038-23103), and 5 cyclopamine (Enzo Life science, Cat. #BML-GR334)]. As a control, osteoblastic differentiation induction described in (1-4) was performed after the embryoid body formation described in (1-2) without mesoderm differentiation induction. For the evaluation of mesoderm differentiation induction, immunofluorescent staining using a mesodermal marker Brachyury was performed. In addition, the embryoid bodies were cultured in a mesoderm differentiation induction medium free of CHIR99021 or cyclopamine to investigate the effects of the two compounds.

(1-4) Induction of Differentiation into Osteoblasts

Figure 5:
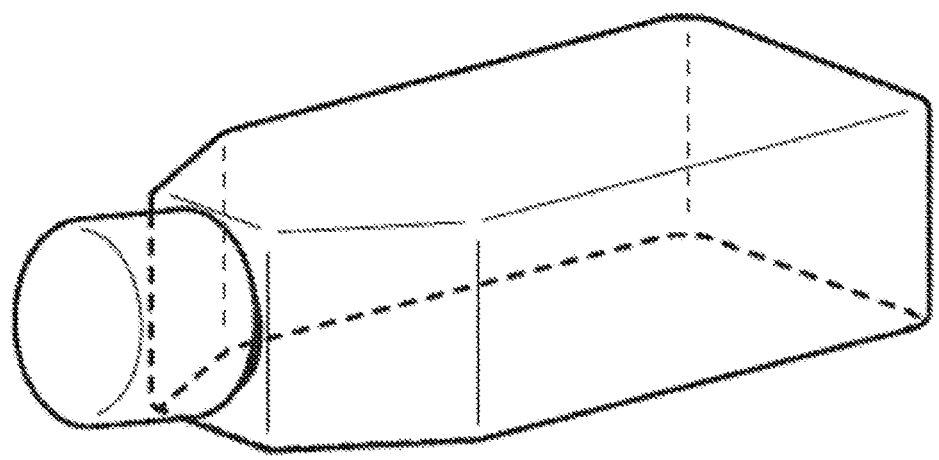
FIG. 5 is a schematic view of a culture flask used in Examples of the present application.

After the mesoderm differentiation induction, the medium was changed to an osteoblastic differentiation induction medium [DMEM medium (sodium pyruvate-free: Nacalai Tesque, Kyoto, Cat. #08459-35) containing 15% FBS (Thermo Fisher Scientific, Cat. #490082), 0.1 µM dexamethasone (Sigma Aldrich, Cat. #D2915), 10 mM β-glycerophosphoric acid (Sigma Aldrich, Cat. #G9422) and 172.7 µM ascorbic acid 2-phosphate (Sigma Aldrich, Cat. #A8960), 100 units/ml penicillin, 100 µg/ml streptomycin, and 250 ng/ml amphotericin B (Thermo Fisher Scientific, Cat. #15240)] to provide a suspension having a cell concentration of from about $1\times10^5$ cells/ml to about $7\times10^5$ cells/ml. The cell suspension was subjected to non-adherent culture for up to 60 days using a low-attachment flask having a shape schematically illustrated in FIG. 5 (Greiner bio-one, Cat. #690195, growth area: 25 cm$^2$) while being shaken on a seesaw bioreactor (10° inclination, cycle: 0.33 Hz, table width: 32 cm, amplitude: 5.5 cm) (BC-700: BIO CRAFT). As a control, non-adherent culture was performed without shaking. The medium was changed every 7 days. The resultant sample was subjected to immunofluorescent staining, specifically hematoxylin and eosin (H&E) staining, von Kossa staining, or Osteocalcin, and subjected to histochemical observation.

In addition, an effect in the case where non-adherent shaking culture was performed with an osteoblastic differentiation induction medium supplemented with a hypoxia-mimetic compound (10 µM desferrioxamine) or a statin compound (1 µM simvastatin) was investigated.

(1-5) Results

Formation of Mesoderm Cell Constructs

In mesoderm cell constructs obtained by the method described in (1-2) and (1-3) above, marked expression of the mesodermal marker (Brachyury) was found (FIG. 1A). In addition, also in the absence of cyclopamine, marked expression of Brachyury was similarly found, and hence induction into mesoderm cell constructs was able to be achieved (FIG. 1B). Meanwhile, in the absence of CHIR99021 (FIG. 1C and FIG. 1D), the expression of Brachyury was found, though not as marked as in the presence of CHIR99021.

Formation of Three-Dimensional Osteoblast Constructs by Stepwise Differentiation Induction Method After embryoid body formation for 1 day had been performed by the method described in (1-1) above, osteoblastic differentiation induction was directly performed without mesoderm differentiation induction. As a result, cells became cellular structures that did not show bag-like mineralization (FIG. 2A).

In view of the foregoing, the effectiveness of a method involving subjecting iPS cells to mesoderm induction before osteoblast induction was investigated. An attempt was made to induce direct differentiation of iPS cells (without embryoid body formation in an ES medium) into mesoderm. As a result, all the iPS cells underwent cell death 1 day after the mesoderm induction (FIG. 2B).

Figure 2:
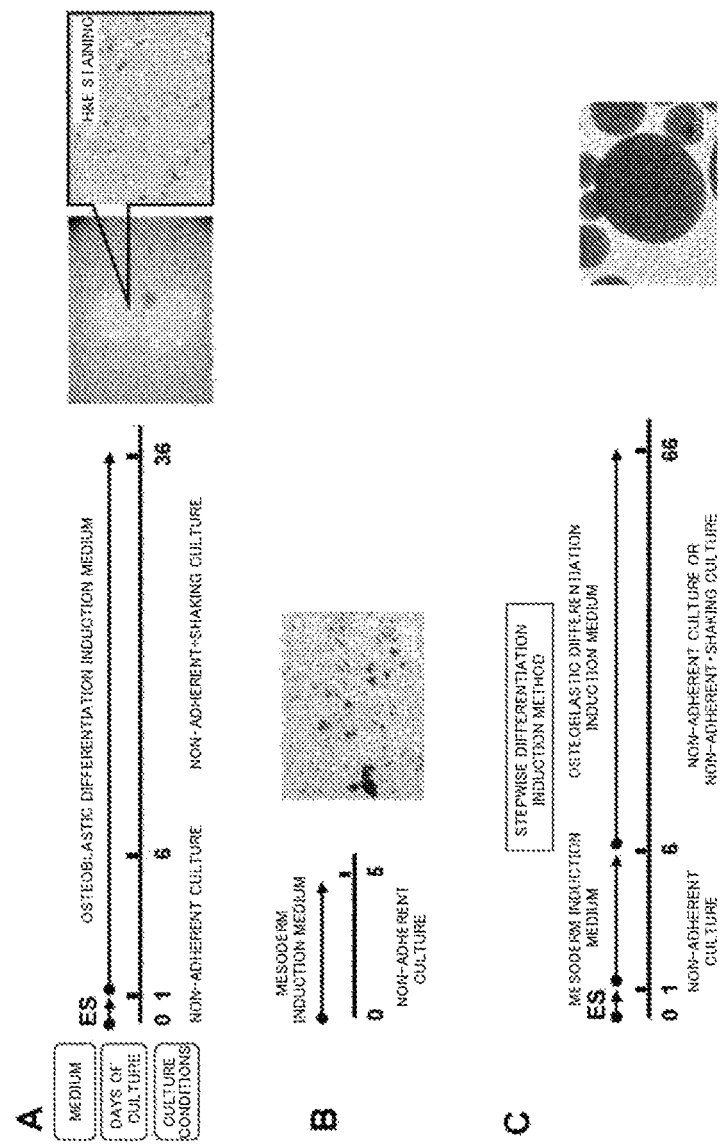
FIG. 2 are diagrams for illustrating the outlines of culture procedures for tests in Examples of the present application and photographs of the resultant cell constructs.

Meanwhile, when embryoid body formation was performed for 1 day and mesoderm differentiation induction was performed for 5 days, followed by osteoblastic differentiation induction, a spherical cell construct was able to be obtained within 60 days from the osteoblastic differentiation induction (FIG. 2C). As a result of histological observation of the cell construct, mineralized portions were found inside the cell construct after the 60 days of the osteoblastic differentiation induction (around Symbol "*" of FIG. 3A). In addition, also when the cell construct was subjected to non-adherent culture without shaking in the osteoblastic differentiation induction step, a mineralized portion was found inside the cell construct (around Symbol "*" of FIG. 3B).

Promotion of Osteoblastic Differentiation with Small-Molecule Compound

Figure 3:
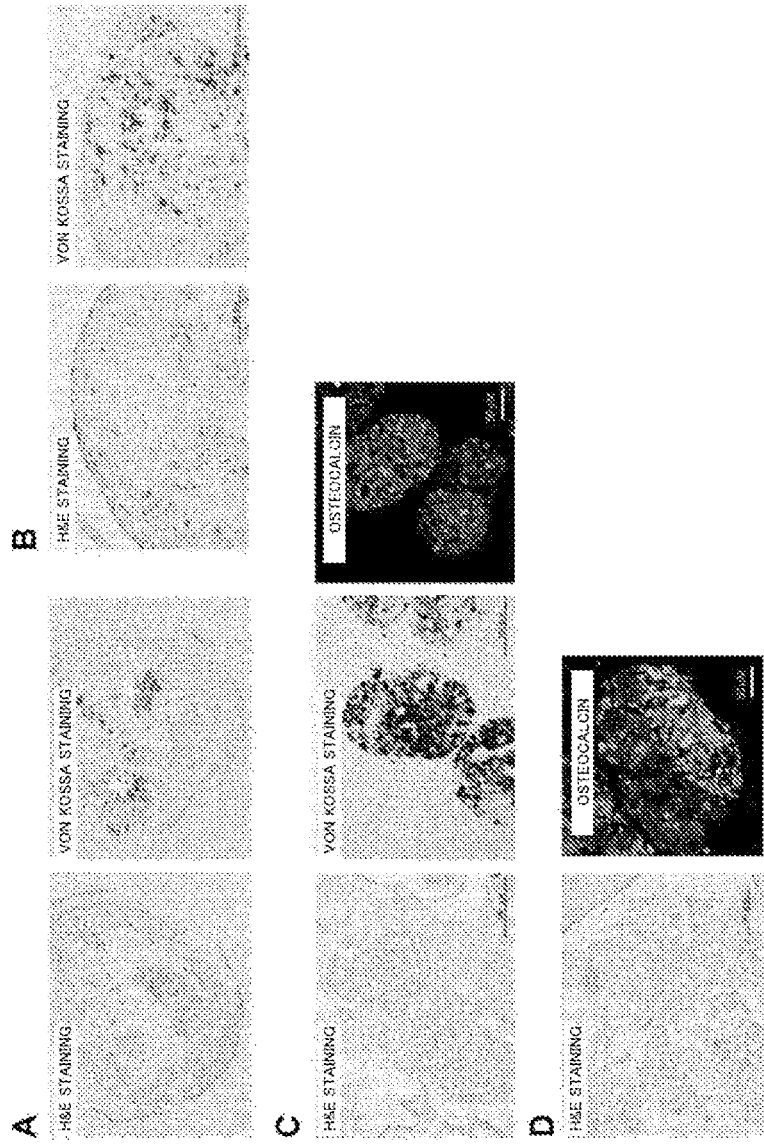
FIG. 3 are photographs for showing the results of immunofluorescent staining, specifically H&E staining, von Kossa staining, or Osteocalcin of osteoblast constructs obtained by tests of a stepwise differentiation induction method in Examples of the present application. A Non-adherent+shaking culture. B Non-adherent culture. C With hypoxia-mimetic compound (desferrioxamine) added. D With statin compound (Simvastatin) added.

As a result of differentiation induction in an osteoblastic differentiation induction medium containing desferrioxamine or simvastatin, a markedly mineralized osteoblast construct was able to be obtained (FIG. 3C and FIG. 3D).

Particularly when desferrioxamine was used, induction into a markedly mineralized cell construct was found on day 30 of the osteoblastic differentiation induction.

(1-6) Method Free of Induction of Differentiation into Mesodermal Cells and Results (Comparative Example)

iPS cells were obtained in accordance with the method described in (1-1) above, and subjected to culture in an ES medium corresponding to (1-2) above for 2 days. The resultant embryoid bodies of the iPS cells were collected, and further cultured for 2 days using the above-mentioned ES medium having blended therein 1 UM retinoic acid (all-trans retinoic acid: Sigma). After that, the step of inducing differentiation into osteoblasts described in (1-4) above was performed without the step of inducing differentiation into mesoderm cells described in (1-3) above. As a result, the resultant osteoblast-like cells were not solid cell constructs, but were bag-like.

(1-7) Conclusion

Thus, it was revealed that the generation of a three-dimensional osteoblast construct from human iPS cells required a stepwise differentiation induction method including the steps for differentiation into an embryoid body and mesoderm cells. In addition, it was revealed that the period of the embryoid body culture in the stepwise differentiation induction method was suitably from 1 day to 3 days. Further, it was shown that the hypoxia-mimetic compound and the statin compound were effective for inducing mineralization of a human iPS cell-derived osteoblast construct.

(2-1) Culture of Human iPS Cells

For an experiment, a human skin fibroblast-derived iPS cell line (409B2: RIKEN BRC CELL BANK) was used. SNLP76.7-4 cells were used as feeder cells.

The SNLP76.7-4 feeder cells were seeded in a 10 cm cell culture plate (coated with 0.1% gelatin), and cultured using a DMEM medium (sodium pyruvate-free: Nacalai Tesque, Cat. #08459-35)] containing 7% fetal bovine serum (FBS: Japan Bio Serum, Lot #JBS-011501), 2 mM L-glutamine (Thermo Fisher Scientific, Cat. #25030-081), 50 U penicillin, and 50 μg/ml streptomycin (Thermo Fisher Scientific, Cat. #15140-122). The medium was changed every 2 days. Before the culture of iPS cells, the SNLP76.7-4 feeder cells were treated with 12 μg/ml mitomycin C (Nacalai Tesque, Cat. #20898-21) for 2.5 hours, and seeded in a 10 cm cell culture plate (coated with 0.1% gelatin) at a concentration of $1.5 \times 10^6$ cells/dish.

iPS cells were seeded on the SNLP76.7-4 feeder cells, and cultured using Primates ES Medium (ES medium: REPROCELL, RCHEOT002, 003) containing 4 ng/ml human basic FGF (REPROCELL, RCHEMD001). The medium was changed every day.

(2-2) Formation of Embryoid Bodies

The iPS cells were washed with phosphate buffered saline (PBS), and treated with 1 ml of a CTK solution (0.25% trypsin, 0.1 mg/ml collagenase IV, 10 mM CaCl2, 20% KSR) at 37° C. for 1 minute. After that, the CTK solution was removed by aspiration, and 1 ml of PBS was added. PBS was removed, and only the feeder cells exfoliated from the culture plate were removed by aspiration as much as possible. After that, adherent iPS cells remaining in the culture plate were collected using 5 ml of an ES medium. The resultant cell suspension was transferred to a low-attachment culture dish (Thermo Fisher Scientific, Cat. #150239), and subjected to non-adherent culture for from 0 days to 4 days to induce the formation of embryoid bodies.

(2-3) Induction of Differentiation into Mesoderm Cells

After non-adherent culture had been performed for from 0 days to 4 days, iPS cell embryoid bodies were collected. The collected iPS cell embryoid bodies were seeded on a fresh low-attachment culture dish and subjected to non-adherent culture for 5 days using 5 ml of a mesoderm differentiation induction medium [1:1 mixed medium of DMEM/F12 (Thermo Fisher Scientific, Cat. #11330-032) and Neurobasal medium (Thermo Fisher Scientific, Cat. #21103-049) containing 2% B-27 Supplement (Thermo Fisher Scientific, Cat. #17504-044), 1% N-2 Supplement (Thermo Fisher Scientific, Cat. #17502-048), 30 CHIR99021 (Wako Pure Chemical Industries, Ltd., Cat. #038-23103), and 5 cyclopamine (Enzo Life science, Cat. #BML-GR334)].

For the evaluation of mesoderm differentiation induction, the expression of a protein of Brachyury serving as a mesodermal marker and the expression of its gene were investigated by immunofluorescent staining and an SYBR Green real-time RT-PCR method, respectively.

The immunostaining was pertained using: anti-Brachyury polyclonal antibody (AF2085, R&D SYSTEMS) as a primary antibody; Alexa Fluor594-labeled anti-goat IgG antibody (Thermo Fisher Scientific) as a secondary antibody; and Hoechst 33258 (Thermo Fisher Scientific) for nuclear staining.

The base sequences of primers used for the SYBR Green real-time RT-PCR method are as shown below. GAPDH was used as an internal control.
Brachury forward primer: 5'-CAGTCAGTACCCCAGCCTGT-3'
Brachury reverse primer: 5'-ACTGGCTGTCCAC-GATGTCT-3'
GAPDH forward primer: 5'-GAAGGTGAAGGTCG-GAGTCA-3'
GAPDH reverse primer: 5'-GAAGATGGTGATGGGAT-TTC-3'

In addition, a mesoderm induction ratio in the case where the embryoid bodies were cultured for 1 day in a mesoderm differentiation induction medium free of CHIR99021 or cyclopamine was investigated using immunofluorescent staining of Brachyury. The mesoderm induction ratio was determined from the ratio of Brachyury-positive embryoid bodies in all embryoid bodies present in an immunostaining photographic image.

(2-4) Induction of Differentiation into Osteoblasts

After the mesoderm differentiation induction, the medium was changed to an osteoblastic differentiation induction medium [DMEM medium (sodium pyruvate-free: Nacalai Tesque, Kyoto, Cat. #08459-35) containing 15% FBS (Thermo Fisher Scientific, Cat #490082), 0.1 μM dexamethasone (Sigma Aldrich, Cat. #D2915), 10 mM β-glycerophosphoric acid (Sigma Aldrich, Cat. #G9422) and 50 μg/ml ascorbic acid 2-phosphate (Sigma Aldrich, Cat. #A8920), 100 units/ml penicillin, 100 μg/ml streptomycin, and 250 ng/ml amphotericin B (Thermo Fisher Scientific, Cat. #15240)], and non-adherent culture was performed for up to 30 days using a low-attachment flask (Greiner bio-one, Cat. #690195, growth area: 25 cm$^2$) with shaking on a seesaw bioreactor (10° inclination, cycle: 0.33 Hz, table width: 32 cm, amplitude: 5.5 cm) (BC-700: BIO CRAFT).

Components of the iPS cell constructs were analyzed using Fourier Transform-InfraRed (FT-IR) spectroscopic analysis. All the iPS cell constructs were collected, fixed with a 10% neutral buffered formalin solution, washed with distilled water, and then gradually dehydrated with ethanol (30%, 70%, 90%, 100%). The ethanol was replaced with fresh ethanol (100%) again, and then the whole was left to stand still in a dryer at 37° C. for 12 hours. The dried cell sample was subjected to FT-IR analysis using a potassium bromide (KBr) plate method. An FT-IR measurement apparatus FT/IR-6300ST (JASCO Corporation) was used for the analysis, and an infrared absorption spectral pattern obtained by 1,000 scans over the range of from 650 cm$^{-1}$ to 4,000 cm$^{-1}$ at a resolution of 2 cm$^{-1}$ was analyzed. As a control, a human freeze-dried bone allograft (FDBA; diameter: 0.25 mm to 1.0 mm: LifeNetHealth) was used.

(2-5) Generation of iPS Cell-Derived Bone Substitute Material

Osteoblast constructs after 120 days of osteoblastic differentiation induction were washed with PBS, and then immersed in 10 ml of PBS at 4° C. overnight. On the following day, the osteoblast constructs were taken out, transferred to a 6 cm cell culture dish, and preliminarily frozen in a freezer at −80° C. overnight. After that, the dish was placed in a freeze dryer (VD-250R; Taitec), and freeze-drying was performed overnight to kill (inactivate) the cells. Thus, an iPS cell-derived bone substitute material was obtained. The dish having placed therein the bone substitute material was covered with a lid, hermetically sealed with a seal, and stored in a moisture-proof storage (glass desiccator).

(2-6) Implantation into Rat Skull Defect Model

A 10-week-old SD rat (Slc:SD; Japan SLC, Inc.) was put under general anesthesia. After that, the scalp was peeled to form a periosteal flap, and a defect having a diameter of 5 mm across the sagittal suture of the skull was formed. The formation of the skull defect was performed using an engine and trephine bar for animal surgery (Implatex, Tokyo, Cat. #04949202) under running water. The freeze-dried iPS cell construct was implanted into the site of the skull defect and covered with the periosteum, and the scalp was sutured. After that, the rat was kept under specific pathogen-free conditions with ad libitum access to water and contact.

(2-7) Results

Figure 6:
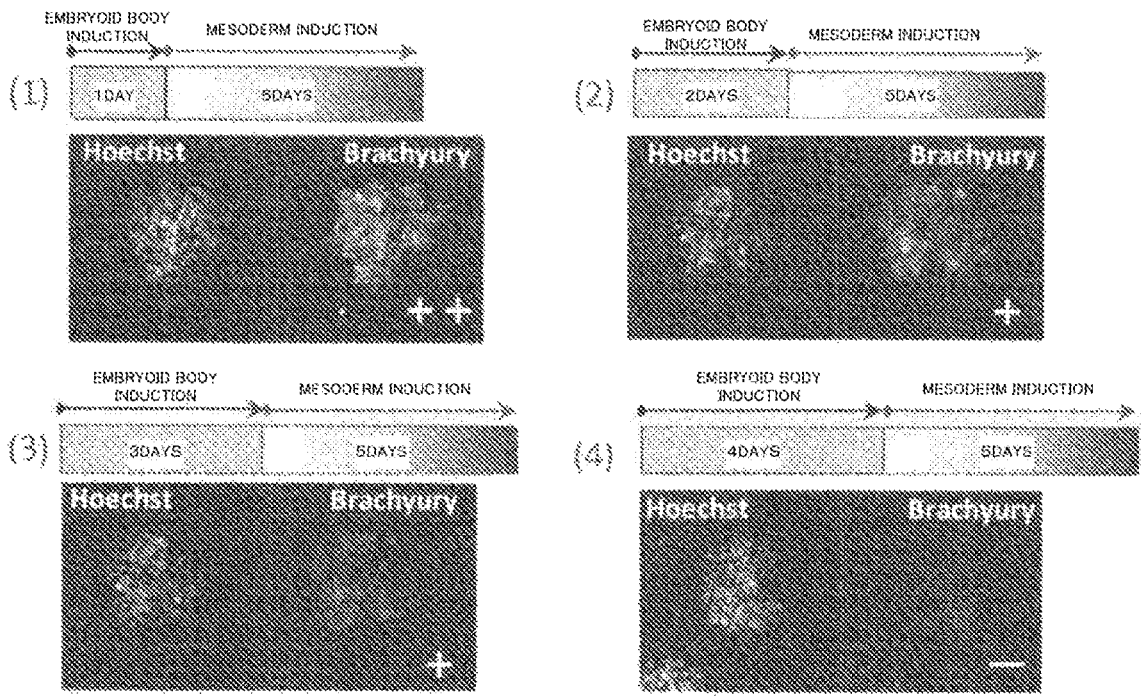
FIG. 6 are photographs for showing the influence of an embryoid body induction period on subsequent mesoderm induction ((Brachyury protein expression)). The results of immunofluorescent staining for evaluating the formation of mesoderm cell constructs in Examples of the present application are shown.

Difference in Formation of Mesoderm Cell Constructs Depending on Embryoid Body Culture Period In the mesoderm cell constructs obtained by the method described in (2-3) above after embryoid body formation for from 1 day to 4 days, a marked reduction in expression of the Brachyury protein serving as the mesodermal marker was found when the embryoid body culture period was 4 days (FIG. 6-(4)). Meanwhile, in the mesoderm cell constructs after having undergone embryoid body formation for from 1 day to 3 days, the expression of the Brachyury protein was increased (FIG. 6-(1) to FIG. 6-(3)). In particular, when the embryoid body culture period was 1 day, the expression of the Brachyury protein was markedly increased (FIG. 6-(1)). Meanwhile, when the non-adherent culture for embryoid body formation induction was performed for 0 days, the cells were killed.

Figure 7:
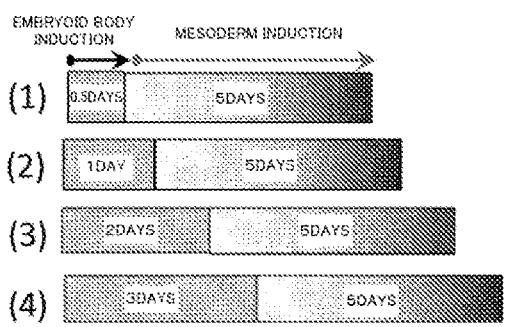
FIG. 7 is a graph for showing the influence of the embryoid body induction period on subsequent mesoderm induction (Brachyury gene expression). A graph of the expression amount of a Brachyury gene in the case where embryoid body induction was performed for various numbers of days, followed by mesoderm induction, in Examples of the present application is shown.
Figure 7:
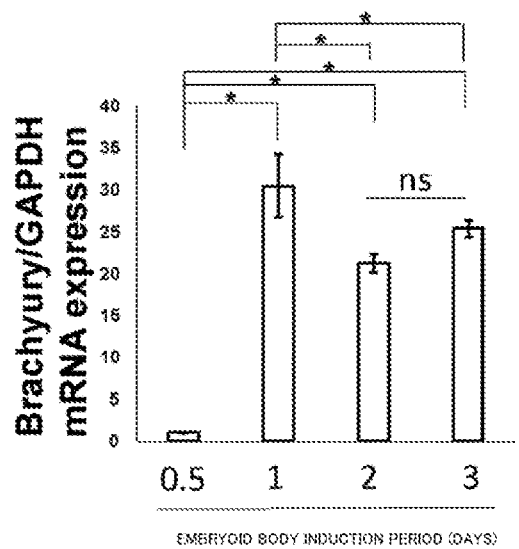

In addition, in the mesoderm cell constructs obtained by the method described in (2-3) above after embryoid body formation for from 0.5 day to 3 days, the expression of the Brachyury gene was increased (FIG. 7). In particular, in the case where the embryoid body culture period was from 1 day to 3 days, the expression of the Brachyury gene was significantly increased as compared to the case of 0.5 day, and in particular, in the case of 1 day, the highest expression was shown (FIG. 7).

Formation of Mesoderm Cell Constructs

Figure 8:
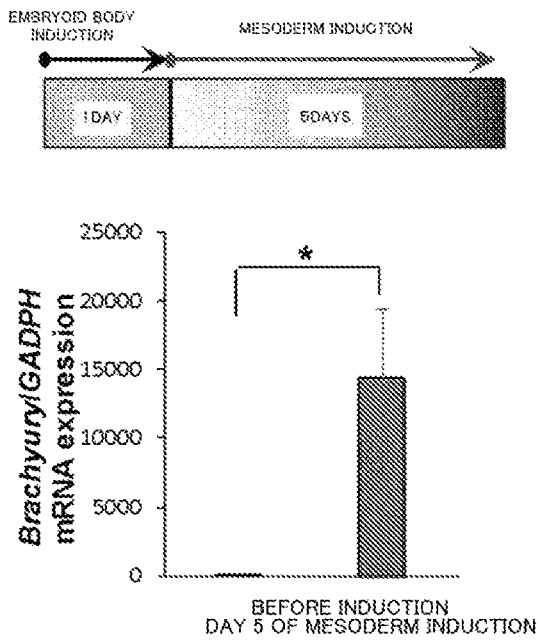
FIG. 8 is a graph for showing the influence of embryoid body induction for 1 day on mesodermal marker gene expressions before and after mesoderm induction. A graph of the expression amounts of the Brachyury gene before and after mesoderm induction in Examples of the present application is shown.
Figure 9:
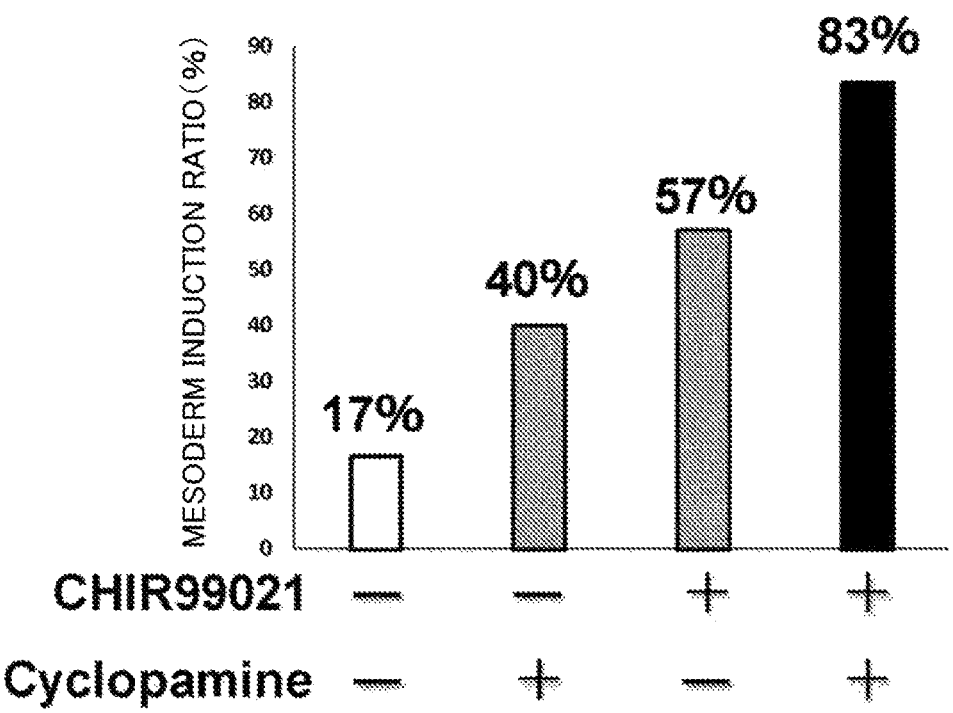
FIG. 9 is a graph for showing the influences of CHIR99021 and Cyclopamine on mesoderm induction. A graph regarding influences on the expression amount of the Brachyury gene in Examples of the present application in the absence of CHIR99021 and cyclopamine is shown.

When embryoid body formation was performed for 1 day and then the induction of differentiation into mesoderm cells was performed by the method described in (2-2) and (2-3) above, the expression of the mesodermal marker (Brachyury) gene in the mesoderm cell constructs after the differentiation induction was increased about 1,500-fold as compared to that before the differentiation induction (FIG. 8). At this time, the mesoderm induction ratio was 83%, and mesoderm induction ratios of 57% and 40% were shown even in the absence of cyclopamine and the absence of CHIR99021, respectively (FIG. 9). In the absence of cyclopamine and CHIR99021, the mesoderm induction ratio was only 17%.

Figure 10:
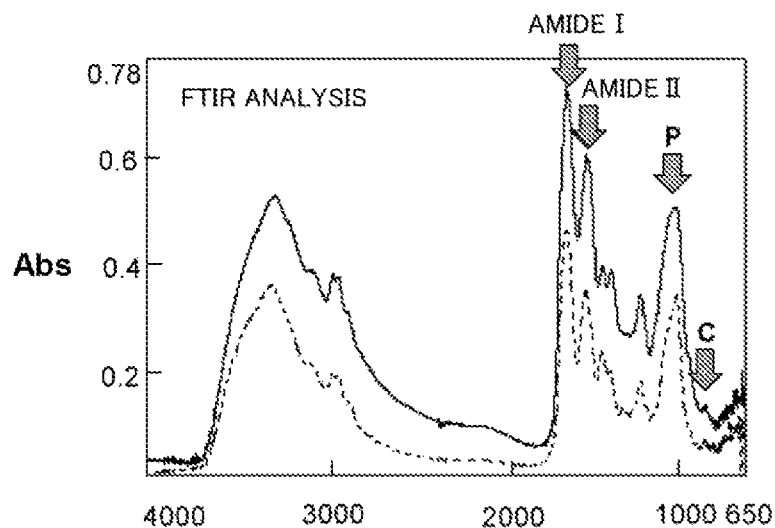
FIG. 10 is a graph for showing a comparison of components of a human iPS cell-derived osteoblast construct and a human freeze-dried bone allograft. FTIR analysis results of a cell construct obtained by osteoblastic differentiation induction and a human freeze-dried bone allograft in Examples of the present application are shown. Solid line: Dried inactivated iPS cell-derived cell construct. Dashed line: human freeze-dried bone allograft (FDBA).

Formation of Three-Dimensional Osteoblast Constructs by Stepwise Differentiation Induction Method Cell constructs obtained by performing embryoid body formation for 1 day, then performing mesoderm differentiation induction, and performing osteoblastic differentiation induction for 30 days were subjected to FTIR analysis. As a result, there appeared peaks suggesting the presence of a phosphate group (P) associated with hydroxyapatite and a carbonate group (C) associated with carbonate apatite in the matrix rich in amino acids (amide I and amide II) (FIG. 10: arrows), and the same infrared absorption spectral pattern as that of a human freeze-dried bone allograft (FDBA) was shown (FIG. 10).

Figure 11:
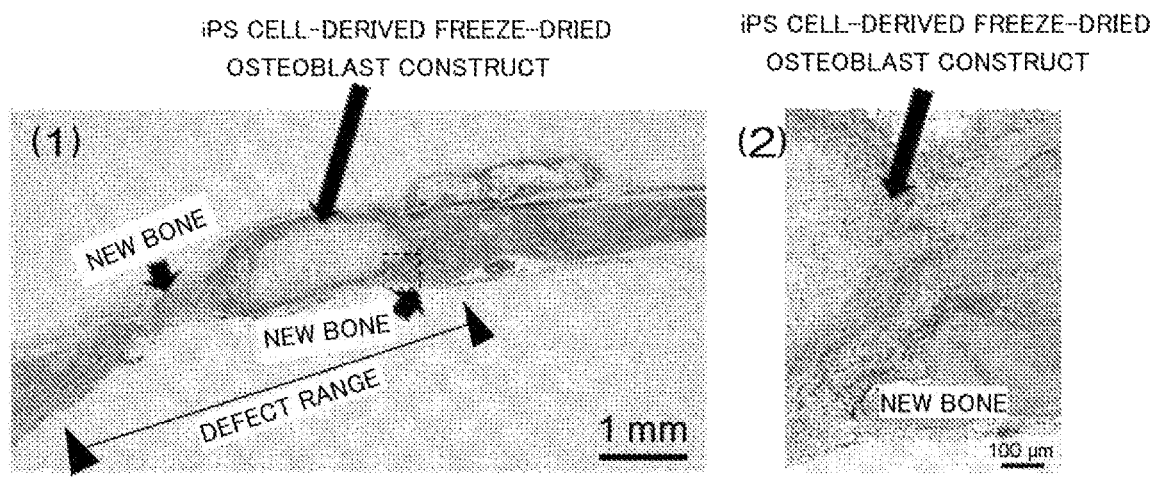
FIG. 11 are photographs for showing the promotion of bone formation using a human iPS cell-derived freeze-dried osteoblast construct. Evaluation results of the bone regeneration ability of a three-dimensional osteoblast construct in Examples of the present application are shown.

Evaluation of Bone Regeneration Ability of Three-Dimensional Osteoblast Construct Generated Using Stepwise Differentiation Induction Method A cell construct on day 120 of osteoblastic differentiation induction was subjected to freeze-drying treatment by the method described in (2-5), and implanted into the site of a bone defect having a diameter of 5 mm generated in the skull of a rat. As a result, the formation of a new bone was found around the freeze-dried osteoblast construct 4 weeks later (FIG. 11-(1) and FIG. 11-(2)). In addition, there was no abnormal finding indicating the accumulation of inflammatory cells or tumorigenesis around the implanted freeze-dried osteoblast construct (FIG. 11-(2)).

(2-8) Conclusion

Thus, it was revealed that the generation of a three-dimensional osteoblast construct from human iPS cells required a stepwise differentiation induction method including the steps for differentiation into an embryoid body and mesoderm cells. In addition, it was revealed that the period of the embryoid body culture in the stepwise differentiation induction method was suitably from 0.5 day to 3 days, most suitably 1 day. In addition, it was revealed that the "human iPS cell-derived freeze-dried osteoblast construct" obtained by freeze-drying the thus produced osteoblast construct to kill (inactivate) the cells had components similar to those of the human freeze-dried bone allograft (FDBA), and promoted the formation of a new bone in the rat skull defect model.

The invention claimed is:

1. A method of producing an osteoblast construct from human induced pluripotent stem (iPS) cells, the method comprising the steps of:
   (1) inducing formation of an embryoid body by subjecting undifferentiated human iPS cells to non-adherent culture for 0.5 day to 3.5 days;
   (2) inducing differentiation of the human iPS cells into mesodermal cells by subjecting the embryoid body of the human iPS cells obtained in the step (1) to non-adherent culture; and
   (3) inducing differentiation into osteoblasts by subjecting the mesodermal cells of the human iPS cells obtained in the step (2) to non-adherent culture, wherein the culture in step (2) is performed in the presence of at least one type of signaling molecule selected from the group consisting of a Wnt signal activator and a Hedgehog signal inhibitor.

2. The method according to claim 1, wherein a culture time in the step (1) is from 0.625 day to 1.25 days.

3. The method according to claim 1, wherein the Wnt signal activator is at least one selected from the group consisting of CHIR99021, 6-bromoindirubin-3'-oxime, kenpaullone, SB-216763, SKL2001, deoxycholic acid, WAY-316606, NSC-693868, ricinine, 7-oxo-β-sitosterol, IM-12, and HLY78.

4. The method according to claim 1, wherein the Hedgehog signal inhibitor is at least one selected from the group consisting of cyclopamine, AY9944, GANT58, GANT61, jervine, SANT-1, SANT-2, U18666A, veratramine, vismodegib, Cur-61414, robotnikinin, JK184, and HPI-4.

5. The method according to claim 1, wherein the culture in the step (3) is performed in the presence of at least one additional component selected from the group consisting of a hypoxia-mimetic compound and a statin compound.

6. A method of producing a bone regeneration agent, comprising the steps of:
producing an osteoblast construct from human iPS cells by;
(1) inducing formation of an embryoid body by subjecting undifferentiated human iPS cells to non-adherent culture for 0.5 day to 3.5 days;
(2) inducing differentiation of the human iPS cells into mesodermal cells by subjecting the embryoid body of the human iPS cells obtained in the step (1) to non-adherent culture; and
(3) inducing differentiation into osteoblasts by subjecting the mesodermal cells of the human iPS cells obtained in the step (2) to non-adherent culture, wherein the culture in the step (2) is performed in the presence of at least one type of signaling molecule selected from the group consisting of Wnt signal activator and a Hedgehog signal inhibitor,
and subjecting the osteoblast construct to inactivation treatment.

* * * * *